US010569391B2

(12) United States Patent
Johnson et al.

(10) Patent No.: US 10,569,391 B2
(45) Date of Patent: Feb. 25, 2020

(54) DRIVER TOOL AND METHOD OF USE

(71) Applicant: ZEST IP HOLDINGS, LLC, Carlsbad, CA (US)

(72) Inventors: James I. Johnson, Temecula, CA (US); Evan A. Cook, Temecula, CA (US)

(73) Assignee: ZEST IP HOLDINGS, LLC., Carlsbad, CA (US)

( * ) Notice: Subject to any disclaimer, the term of this patent is extended or adjusted under 35 U.S.C. 154(b) by 155 days.

(21) Appl. No.: 15/463,965

(22) Filed: Mar. 20, 2017

(65) Prior Publication Data

US 2017/0282337 A1    Oct. 5, 2017

Related U.S. Application Data

(60) Provisional application No. 62/318,479, filed on Apr. 5, 2016.

(51) Int. Cl.
*B25G 1/10* (2006.01)
*B25B 15/00* (2006.01)

(52) U.S. Cl.
CPC ............ *B25B 15/004* (2013.01); *B25G 1/102* (2013.01)

(58) Field of Classification Search
CPC . B25B 15/004; Y10T 29/53596; Y10T 29/54; Y10T 29/53909
See application file for complete search history.

(56) References Cited

U.S. PATENT DOCUMENTS

| 6,419,489 | B1 | 7/2002 | Jorneus et al. | |
| 6,575,057 | B1 | 6/2003 | Ploeger et al. | |
| 6,601,482 | B2 | 8/2003 | Hughes et al. | |
| 2013/0205954 | A1* | 8/2013 | Lukes | B25B 15/004 81/436 |
| 2014/0331826 | A1* | 11/2014 | Campbell | F16B 23/003 81/436 |

OTHER PUBLICATIONS

International Search Report and Written Opinion dated Jul. 5, 2017, ISA/KR based on corresponding PCT application PCT/US2017/023227 (9 pages).

* cited by examiner

*Primary Examiner* — David P Bryant
*Assistant Examiner* — Amanda Kreiling
(74) *Attorney, Agent, or Firm* — Procopio, Cory, Hargreaves & Savitch LLP

(57) ABSTRACT

A driver tool for insertion and removal of a first part configured for threaded engagement in a corresponding threaded bore in a second part has a driving end portion of polygonal shape with multiple flats configured for engagement in a recess in the first part having a corresponding polygonal shape. Some or all of the flats have a respective grabbing feature or edge designed to grab or grip into the opposing surface of the recess to allow a greater amount of torque to be applied to the first part when the tool is rotated in the unthreading direction than when it is rotated in the opposite threading or insertion direction.

11 Claims, 6 Drawing Sheets

DRIVER TOOL AND METHOD OF USE

RELATED APPLICATIONS

This application claims the benefit of Provisional Application No. 62/318,479, filed on Apr. 5, 2016, and the contents of the aforementioned application are incorporated herein by reference in their entirety.

BACKGROUND

Field of the Invention

Devices and methods provided herein relate to a driver tool for threading and unthreading of a part into and out of a threaded bore in another part, and are particularly concerned with hexagonal or other polygonal driver tools for threading and unthreading parts of a dental attachment assembly or the like.

Related Art

Dental attachment assemblies are known in which a dental attachment device or retention member has a threaded portion at one end releasably secured in a cap or denture attachment housing and a snap engaging formation at the other end for releasable snap engagement with an abutment attached to a tooth root or implant. For example, U.S. Pat. Nos. 9,452,029 and 9,486,300 describe a removable ball or retention member which has a first end threadably attached in a cap or denture attachment housing and a retentive head or ball at a second end for releasable snap engagement in a socket of a mating abutment. The retentive head or ball in such devices typically has an indent at its outer end which is of polygonal shape for engagement by a driver tool with an end portion of corresponding polygonal shape and dimensions for mating engagement in the indent in order to apply torque to thread the removable ball into a matching threaded bore at the inner end of a cavity in the denture attachment housing. Typically such driver tools are hex drivers with end portions of hexagonal shape substantially matching a hexagonal bore in the end of the part. The retention member is of compressible material such as plastic or a soft metal, and may need to be removed and replaced periodically due to wear. Another issue with such devices is that the hex end of a conventional hex driver tool can damage the hex indent if excessive force is applied during insertion. In some cases, the removal torque required to remove the component when worn or damaged exceeds the capability of a conventional hex driver.

Therefore, it is desirable to provide a tool which limits the amount of torque applied during threading of a retention member into a denture attachment housing, or during engagement with similar parts to be threaded into such devices.

SUMMARY

Embodiments described herein provide for a driver tool for insertion and removal of a retention member or other similar part of a dental attachment assembly having a threaded end portion configured for threaded engagement in a corresponding threaded bore in a denture attachment housing which is integral with or secured in a dental prosthesis. In one aspect, the driver tool has a handle portion and a shaft extending from the handle portion which has a driving end portion of polygonal shape with multiple flats extending to an outer end face of the tool and configured for engagement in a recess in a compressible part having a corresponding polygonal shape. One or more of the flats has a grabbing feature or edge extending along part of the length of the flat from the end face along at least part of the length of the driving end portion. In some embodiments, each flat has a grabbing feature or edge. The polygonal shape of the driving end portion may be a hexagon with six flats, but other polygonal shapes may be used in alternative embodiments. In some embodiments, each flat has a cut or indent of substantially triangular cross-section or V-shape extending along at least part of the driving end portion, and one side of the indent forms the grabbing feature which in this case comprises a sharp edge between the outer end of the one side of the indent and an adjacent flat.

In one aspect, the cuts or indents are arranged at the left hand sides of each flat as viewed in the direction towards the outer end face of the driving end portion, with the left and right hand side faces of the cut being at different angles to the flat and meeting at the inner end of the cut to form a V-shape, whereby the indent is of generally triangular cross-section.

In one aspect, the arrangement of the indents is such that a respective grabbing edge or feature is created at one side of each indent at the junction between the indent and the next adjacent flat of the driving end portion of tool. Each grabbing feature has a sharp edge which is designed to engage an opposing flat of the recess when the tool is rotated in the clockwise, threading direction or the counter-clockwise or unthreading direction, when the engagement forming a larger angle when the tool is rotated in the anti-clockwise unthreading direction than when the tool is rotated in the clockwise or insertion direction.

In one embodiment, when the driving end portion is engaged in a tool-receiving recess of a first part to be threaded into a second part and is rotated in a clockwise direction relative to the part, the tool engages opposing flats of the recess at a very shallow angle between the driver grabbing features or edges and respective flats of the recess. In one embodiment, the engagement angle is of the order of one to three degrees, so that a limited amount of torque is applied in the clockwise direction to thread the threaded end portion of the part into a matching threaded bore in the second part. When the driving end portion is rotated in the counter-clockwise direction in order to unthread or unscrew the part from the second part for replacement purposes when the part is worn or damaged, the angle between the face of the indent which forms the grabbing feature or edge and the opposing surface of the recess at the point of contact between the grabbing edge and recess is relatively large, and larger than the shallow angle formed between the flat of the tool and the opposing flat of the recess when the tool is rotated in the threading direction. The arrangement is such that the series of grabbing features or edges along one side edge of each indent bite into the compressible material of the respective flats of the recess with greater force when the driver is rotated in an unthreading direction than when it is rotated in a threading direction, allowing the driver to apply a higher amount of torque to unthread the first part from a second part than when it is used for threading the first part into the second part. In one embodiment, the angle between the grabbing feature or edge of the indent and the opposing flat of the recess may be over 25 degrees when the tool is rotated in the unthreading direction, and in one specific example the angle is 34 degrees. This helps in removal of damaged or worn parts which may have uneven or damaged flats in the tool engaging recess, while reducing the risk of damage when a new first part is threaded into the second part.

Other features and advantages of the present invention will become more readily apparent to those of ordinary skill in the art after reviewing the following detailed description and accompanying drawings.

BRIEF DESCRIPTION OF THE DRAWINGS

The structure and operation of the present invention will be understood from a review of the following detailed description and the accompanying drawings in which like reference numerals refer to like parts and in which.

DETAILED DESCRIPTION

Figure 1:
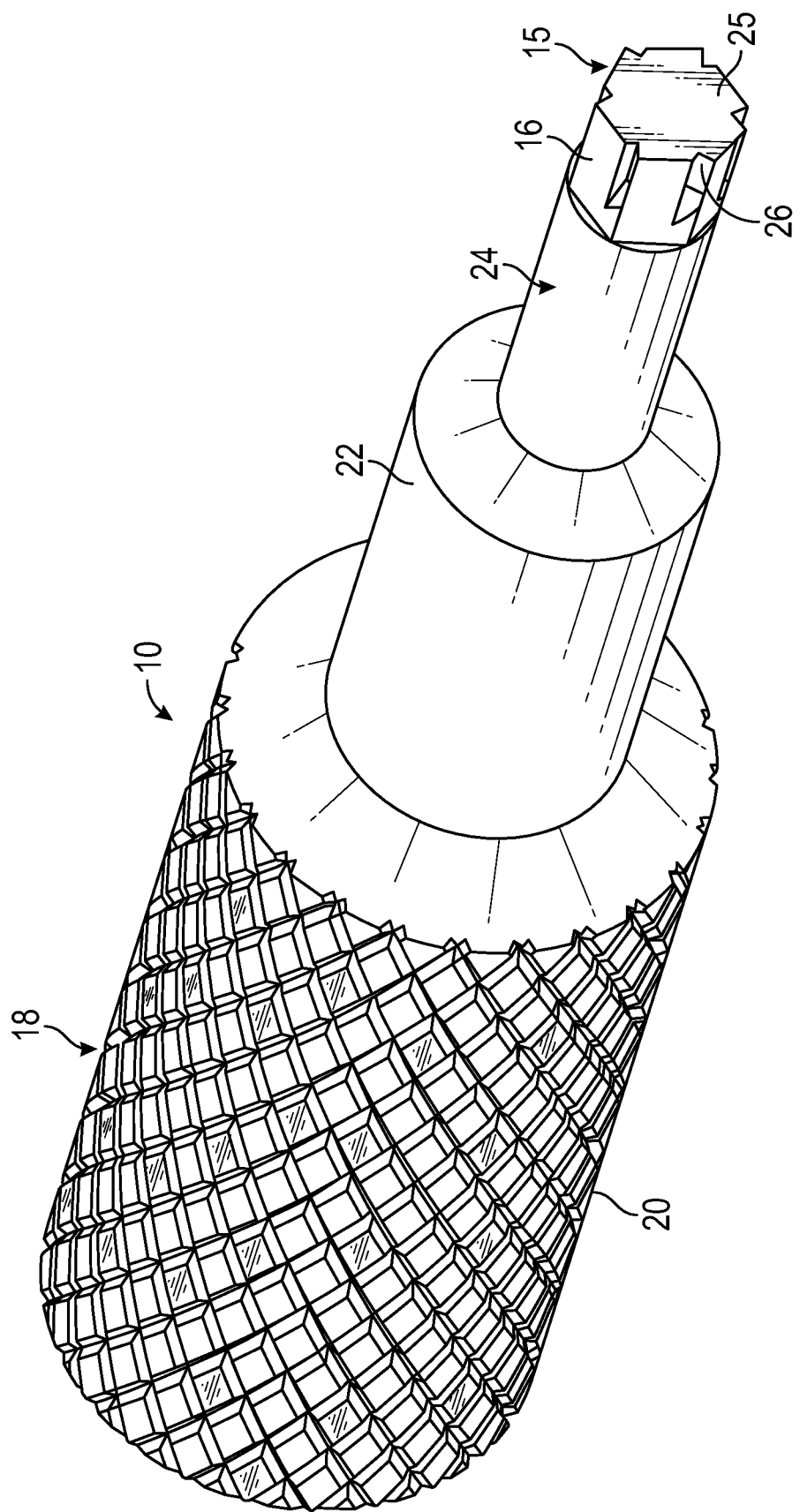
FIG. 1 is a perspective view of a driver tool according to one embodiment.
Figure 2:
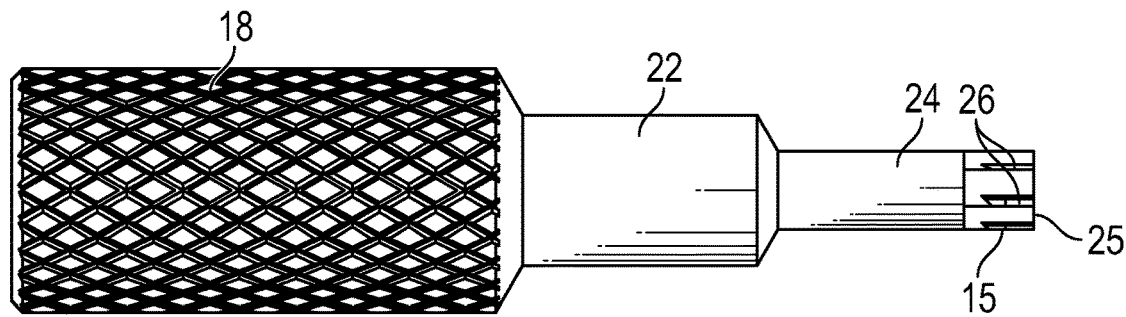
FIG. 2 is a side elevation view of the driver tool of FIG. 1.
Figure 3:
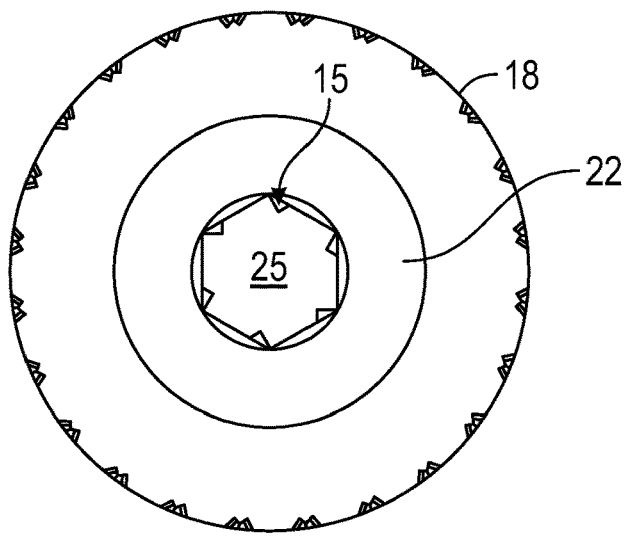
FIG. 3 is an end elevation view of the driver tool of FIGS. 1 and 2, showing the outer end face of the driver portion of the tool, according to one embodiment of the invention.

Certain embodiments disclosed herein provide for a polygonal or hex driver tool configured for engagement with a recess in a compressible part, such as a retention member or retention ball of a dental attachment assembly, so as to rotate the part in one direction to thread a threaded portion of the part into a housing or second part, and to rotate the part in an opposite direction to unthread it and remove it from the housing when replacement is needed. The driver tool is designed with grabbing features or edges which apply more torque on the compressible part in the unthreading direction than in the threading direction.

After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention as set forth in the appended claims.

The present invention relates to a driver tool for use with dental parts such as parts of a dental attachment assembly as described below, but it will be understood that the driver tool may also be used in any other application where a hex driver tool or tool with any polygonal driving end portion is used to engage a plastic or compressible part in order to thread the part into engagement with another part or to release it from the part.

FIGS. 1 to 5 illustrate one embodiment of a driver tool 10 for engagement in a recess in a part of a dental attachment assembly (or other system) in order to thread the part into engagement with another device or remove it from the device when replacement is needed. In one embodiment, the member is a retention member or retention ball 12 configured for threaded engagement with a denture attachment housing or cap 14 which is either integral with or secured in a dental appliance or prosthesis, as illustrated in FIG. 6. FIGS. 7 to 14 illustrate one embodiment of operation of the tool 10 to thread retention ball 12 into cap 14 and to remove it from the cap 14 if replacement is needed. In one embodiment, the driver tool 10 is of suitable dimensions for engagement with the retention ball or retention member of the system described in U.S. Pat. No. 9,486,300, the contents of which are incorporated herein by reference, or other similar dental systems. However, the driver tool may be used in fields outside dentistry for engagement with other compressible pieces of plastic, softer metals or the like which are designed for threaded engagement with other parts.

As illustrated in FIGS. 1 to 5, driver tool 10 is a hex driver with a driving end portion or tip 15 of hexagonal cross-sectional shape with six flats or flat faces 16, but it will be understood that similar driver tools may be provided with different numbers of flats for engagement in recesses of different polygonal shapes. Tool 10 has handle 18 at one end which has a gripping surface 20 with a grooved pattern, and a shaft 22 extending from handle 18 and having a reduced diameter shaft portion 24 terminating in the hexagonal driver portion or tip 15.

Figure 4:
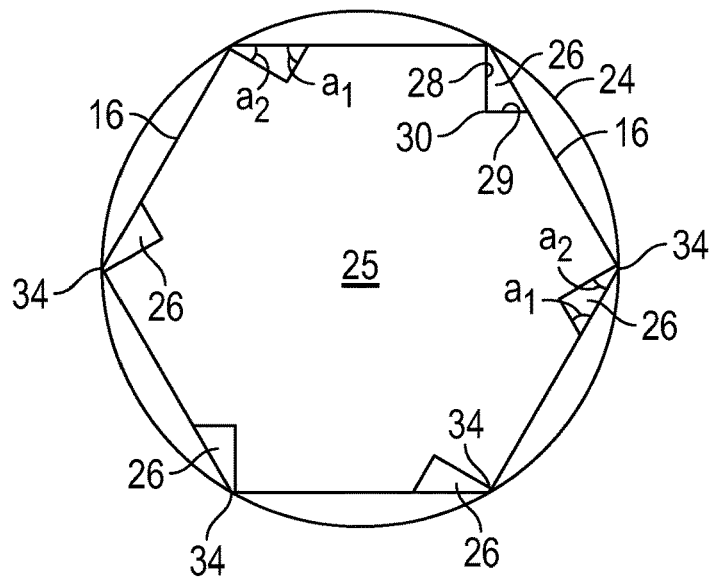
FIG. 4 is an enlarged end view of the tip or driving end portion of the driver tool of FIGS. 1 to 3, illustrating the cut surfaces or indents on the tip.
Figure 5:
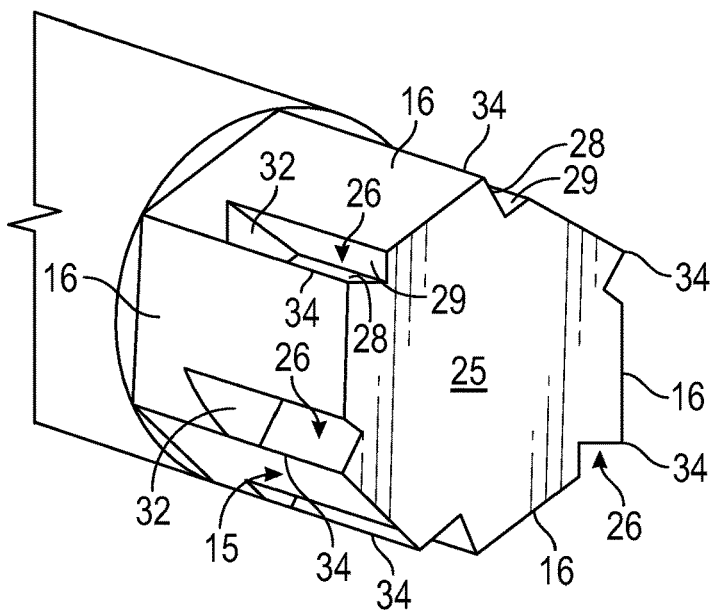
FIG. 5 is an enlarged perspective view of the tip or driving end portion of the driver tool of FIGS. 1 to 4, illustrating the shape of the cut grabbing features in more detail.
Figure 6:
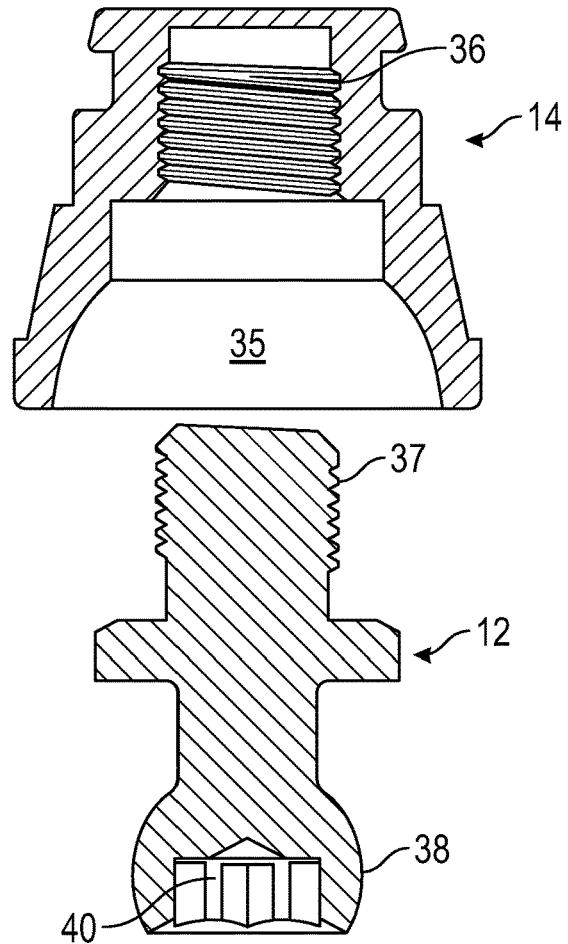
FIG. 6 is an exploded longitudinal cross-sectional view of the separated parts of a prior art dental attachment assembly.
Figure 7:
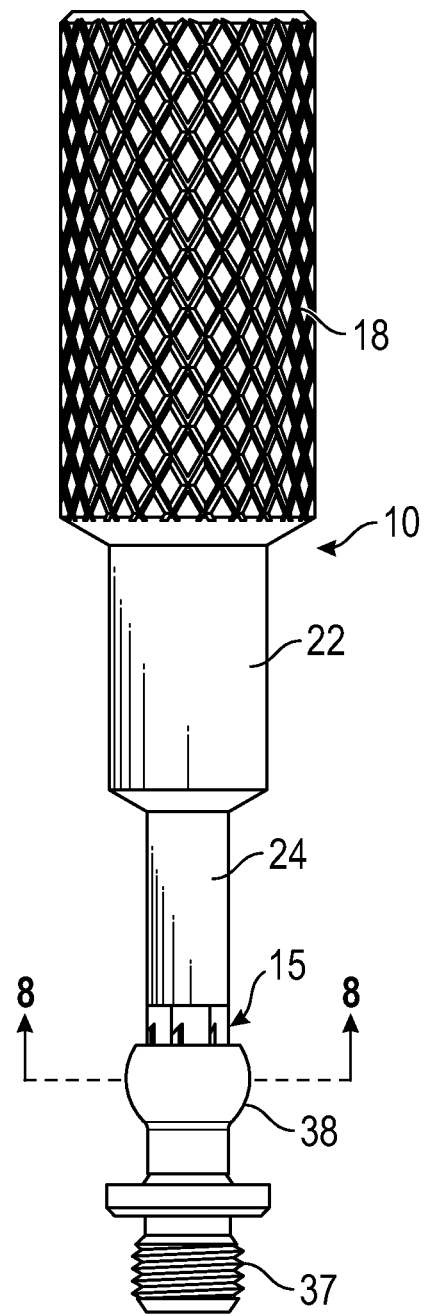
FIG. 7 is a side elevation view illustrating the tip or driving end portion of the tool engaging in the hexagonal recess in the end of the retention member of the denture attachment assembly of FIG. 6.
Figure 8:
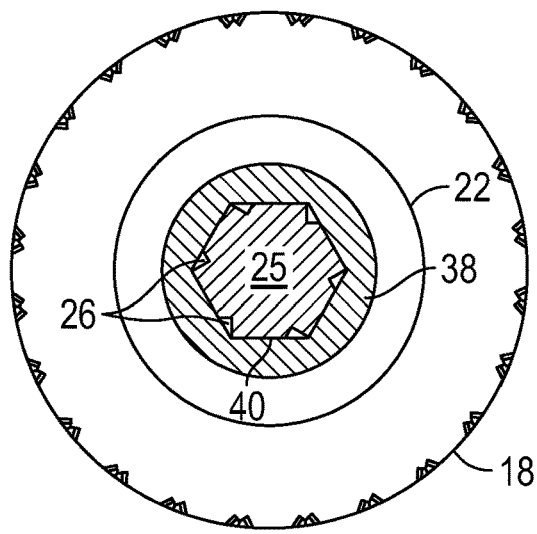
FIG. 8 is a cross-section on the lines 8-8 of FIG. 7 on an enlarged scale, illustrating the end of the tool engaging in the corresponding hex recess in the retention member or part.

Tip 15 has a flat outer end face 25, and each flat surface 16 has a cut or indented recess 26 of generally triangular shape extending along a left hand side portion of the flat surface from the outer end face 25 along at least part of its length, as best illustrated in FIGS. 4 and 5. One cut or indented recess 26 is illustrated in more detail in FIG. 5, with all other cuts being identical. As illustrated, the cut has opposite angled side faces 28, 29 terminating at a point 30 at the innermost end of the recess, and the cut terminates at end wall 32. The two side faces are at different angles to the respective flat surface 16 in which the cut or indent is located, as illustrated at $a_1$ and $a_2$ in FIG. 4, where $a_1 > a_2$. This cut or indent forms a grabbing feature or edge 34 at the junction between the outer side of the indent and the next flat face 16. Grabbing features or edges 34 operate to "grab" or dig into an opposing face of a hexagonal recess in a part engaged by tip 15 with greater force when the tip is rotated in an anti-clockwise or counter-clockwise direction (as viewed in a direction into the recess, i.e. a direction out of the paper in FIG. 4) to produce a higher amount of torque during removal than during insertion, where the tool is rotated in the clockwise direction. This is described in more detail below with reference to FIGS. 7 to 15.

Although each flat of the driving end portion of the tool has a recessed indent forming a grabbing feature or edge in the illustrated embodiment, some flats may have no indent or grabbing features in alternative embodiments, depending on the amount of torque required. For example, a grabbing feature may be provided only one flat, two opposite flats, or alternating flats in some embodiments. The shaft 22 of hex driver 10 may be made of any suitable hard and strong material, such as high strength tool steel or the like. The dimensions are varied dependent on the dimensions of the hex recess in the part in which it is intended to engage. In one example, the size of the hexagonal driving feature across end face 25 was 1.25 mm. measured between two diametrically opposing flats, but the same grabbing features may be provided on a polygonal driver tool of any dimensions.

FIG. 6 illustrates two parts of a dental attachment assembly for use in attaching a dental prosthesis to a tooth root or implant, comprising a denture attachment housing or cap 14 which may be integral with or secured into a recess in a dental prosthesis, and a retention member or retention ball 12 for releasable attachment to cap or housing 14. The housing 14 has an outwardly facing cavity 35 and a threaded bore 36 at an inner end of the cavity. Retention member 12 has a threaded shaft 37 at one end for releasable threaded engagement in bore 36 and a part spherical head 38 at the opposite end for snap engagement in a recess in an abutment (not illustrated) of the dental attachment assembly which is secured to a tooth root or implant. As illustrated, the outer end of the head has a hexagonal recess 40 for engagement with a suitable matching tip of a driver tool for engaging threaded shaft 37 into matching threaded bore 36. It will be understood that this is just one example of parts which may be engaged or released using the driver tool, with appropriate adjustment of the dimensions of the driving end portion according to the dimensions of the recess in which it is to be engaged.

Figure 9:
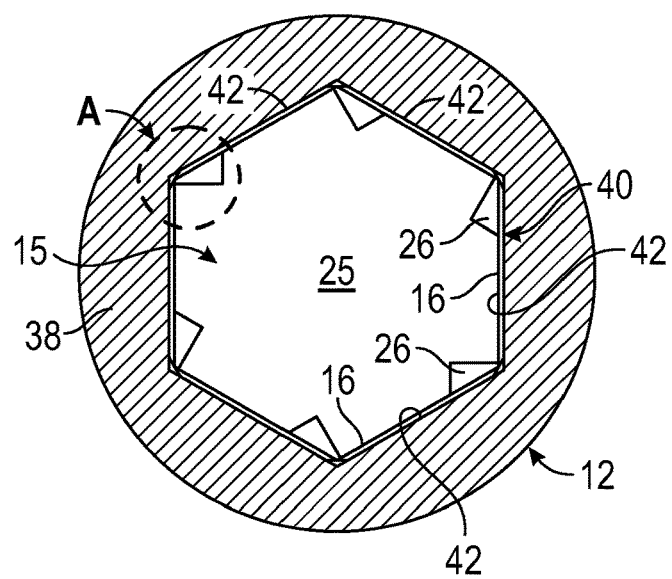
FIG. 9 is a close up view of the engagement of the driver in the tool engaging recess of the retention member as seen in FIG. 8, prior to application of any torque.
Figure 10:
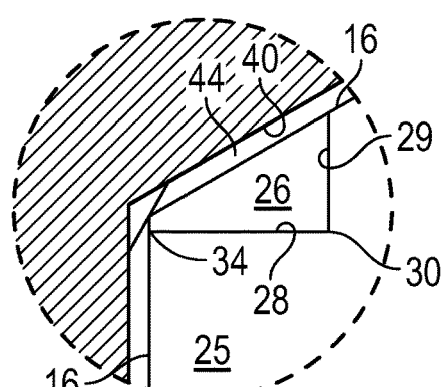
FIG. 10 is an enlarged view of the circled area labeled A in FIG. 9, illustrating the space between one of the cuts or grabbing features of the driver portion and the corresponding tool engaging recess of the retention member in the relative orientation of FIG. 9, when there is no torsional load between the driver and retention member.

One embodiment of a method of using driver tool 10 to secure retention member 12 to denture attachment housing 14 and to remove the retention member from the housing is described below in more detail, with reference to FIGS. 7 to 14. FIGS. 7 to 10 illustrate the tip 15 of the driver or driver tool 10 inserted into the matching recess 40 in the retention head 14 prior to application of any driving torque, as it is initially engaged for insertion or removal of the retention head. In this position, the driver flats 16 are parallel with the corresponding flats 42 of recess 40 in retention ball or part 12. As illustrated in FIGS. 9 and 10, in this position there is a gap 44 between the driver flats and recess flats, the grabbing features 34 are not engaged with the recess, and there is no torsional load between the driver and retention ball.

Figure 12:
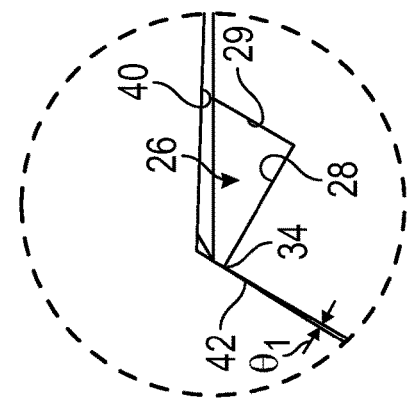
FIG. 12 is an enlarged view of the circled area labeled 12 in FIG. 11, illustrating engagement of the grabbing feature of the driver portion with the opposing flat in the retention ball recess.
Figure 11:
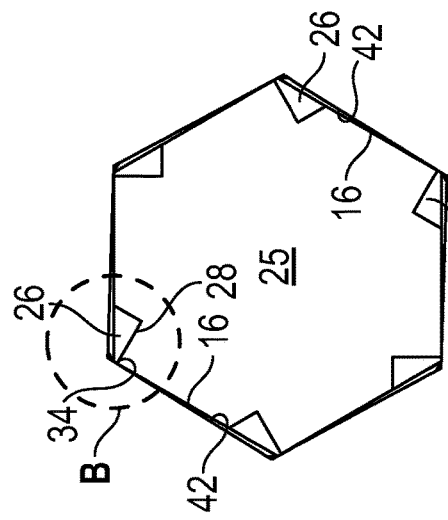
FIG. 11 is a close up view similar to FIG. 9, but illustrating application of torque in a clockwise direction (as viewed in a direction into the recess or out of the page) to thread the retention member into the threaded bore of the denture attachment housing or cap of a dental attachment system.

FIG. 11 is an end view illustrating the driver rotated relative to recess 40 in a clockwise direction (as viewed in a direction out of the paper) in order to screw the retention ball into the denture attachment housing of the dental attachment system, while FIG. 12 is an enlargement of the circled area B in FIG. 11 illustrating the engagement of one of the grabbing features or edges 34 with an opposing flat 42 of recess 40. As illustrated in FIG. 12, the engagement angle $\theta_1$ between the respective driver face 16 adjacent grabbing feature or edge 34 and the opposing flat 42 of the retention ball recess at the point of contact between each grabbing feature 34 and flat 42 is very small. In one embodiment, angle $\theta_1$ is less than ten degrees, and in one example the angle is around two degrees. The shallow angle only allows the edge 34 to bite into the opposing flat of the recess by a small amount, so the hex driver is only able to apply a limited amount of torque in the clockwise direction in order to screw the threaded portion 37 of the retention ball into housing 14. When the torque limit is reached, the driver expands the plastic causing a ratcheting type action as the driver rotates within the recess.

Figure 14:
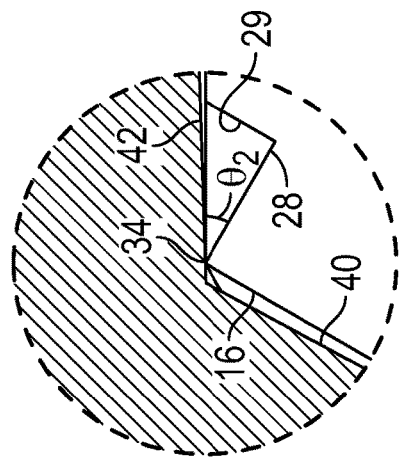
FIG. 14 is an enlarged view of the circled area labeled C in FIG. 13, illustrating engagement of one of the grabbing features with opposing flat of the retention ball recess.
Figure 13:
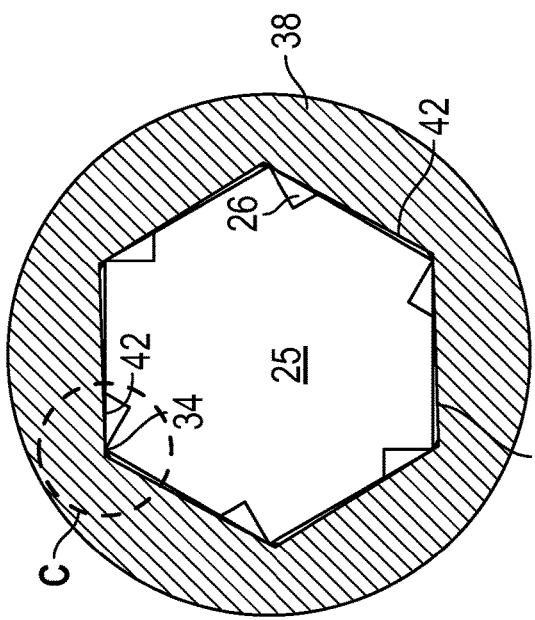
FIG. 13 is a close up view similar to FIG. 11, but illustrating application of torque in a counter-clockwise direction (as viewed from a direction into the recess or out of the page) to unthread the retention member out of the threaded bore of the denture attachment housing or cap of a dental attachment system.

FIG. 13 is an end view illustrating the driver rotated relative to recess 40 in an counter-clockwise direction (as viewed in a direction out of the paper) in order to unthread or unscrew the retention ball from the denture attachment housing of the dental attachment system, while FIG. 14 is an enlargement of the circled area C in FIG. 13 illustrating the engagement of grabbing feature or edge 34 with an opposing flat 42 of recess 40. As illustrated in FIG. 14, rotation in a counter-clockwise direction causes the edge 34 to engage the opposing flat 42 of the recess at an angle $\theta_2$ between the indent face 28 and the opposing flat 42 of the retention ball recess at the point of contact between grabbing feature 34 and flat 42. In one embodiment, angle $\theta_2$ is greater than 25°, and in one example the angle is around 34 degrees. The larger angle causes the edge 34 of each cut or indent 26 to bite more into the retention ball material, e.g. plastic or the like, grabbing the retention ball and allowing the hex driver to be able to apply a higher amount of torque in the counter-clockwise direction before the torque limit is reached, so that the threaded portion 37 of the retention ball can be unscrewed in order to release the retention ball from housing 14.

The driver tool described above has the advantage that the same tool and the same driving end of the tool can be used to apply both insertion (or tightening) torque and removal or loosening torque, and that the tool has the ability to apply a greater amount of torque in the removal or counter-clockwise direction than in the insertion or clockwise direction. This increases the ability of the clinician to remove the retention ball from the dental attachment housing if it is damaged and needs replacement, and also reduces the risk of excessive force being applied during insertion. It will be understood that a driver tool of appropriate dimensions having the same or similar indents or cuts may be used in other applications in dental or other fields in order to engage a recess in a part to be threaded into or unthreaded from another part, particularly in the case of compressible parts of materials such as plastic, soft metal and the like. Additionally, driver tools having greater or fewer grabbing features or edges may be provided in other embodiments.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly limited by nothing other than the appended claims.

What is claimed is:

1. A driver tool for threading a first part into a threaded bore of a second part and unthreading the first part from the threaded bore, comprising:

an elongate member having a handle at a first end and a shaft extending from the handle and having a driving end portion of polygonal cross-sectional shape having an outer end face and an outer surface having multiple flats extending up to the outer end face and configured for engagement in a recess in a first part which is of substantially matching polygonal cross-sectional shape;

one or more flats of the driving end portion each having a grabbing feature extending along at least part of the length of the driving end portion from the outer end face, which is configured to engage a respective opposing flat of the recess when the driver is rotated in opposite clockwise and counter-clockwise directions relative to the recess, wherein the grabbing feature is configured to bite into the respective opposing flat of the recess and apply a greater amount of torque to the first part when the driver is rotated in a counter-clockwise, unthreading direction than when it is rotated in a clockwise, threading direction relative to the recess, wherein each of the one or more flats is formed as a triangular cut in a flat face of the polygonal cross-sectional shape of the driving end portion of the shaft of the elongate member, each cut defining a pair of flat faces angled with respect to the flat face of the polygonal cross-sectional shape of the driving end portion of the shaft of the elongate member and the pair of flat faces forming an angle.

2. The driver tool of claim 1, wherein each flat of the driving end portion has a grabbing feature.

3. The driver tool of claim 2, wherein each flat of the driving end portion has an indent extending along at least part of the driving end portion from the outer end face, the indent having opposite first and second side faces extending from an inner end of the recess up to the outer surface, the first side faces of each indent forming an edge between the first side face of the indent and an adjacent flat of the driving end portion, the edge comprising said grabbing feature.

4. The driver tool of claim 3, wherein the second side face of the indent extends from the inner end to the respective flat of the driving end portion in which the indent is located and the first side face of the indent extends from the inner end to an adjacent flat of the driving end portion.

5. The driver tool of claim 3, wherein the indent is generally V-shaped in cross-section and the first face of the indent has a cross-sectional length greater than the cross-sectional length of the second face.

6. The driver tool of claim 3, wherein an angle θ1 between the adjacent flat to the grabbing feature and the opposing flat of the recess when the driver is rotated in a clockwise, threading direction is less than an angle θ2 between said first side face of the indent and the opposing flat of the recess when the driver is rotated in an anti-clockwise, unthreading direction.

7. The driver tool of claim 6, wherein θ1 is less than ten degrees and θ2 is greater than twenty five degrees.

8. The driver tool of claim 7, wherein θ1 is approximately 2 degrees and θ2 is approximately 24 degrees.

9. The driver tool of claim 1, wherein the driving end portion is of hexagonal cross-sectional shape.

10. The driver tool of claim 1, wherein the driving end portion is shaped and sized to fit into and engage in a tool engagement bore of polygonal shape in a retention member of a denture attachment assembly which has a threaded end portion for threaded engagement in a mating threaded bore of a denture attachment housing.

11. The driver tool of claim 1, wherein the shaft has a first, larger diameter portion extending from the handle, and a reduced diameter portion extending from the first, larger diameter portion and terminating in said driving end portion of polygonal shape.

* * * * *